US012310906B2

(12) United States Patent
McKenney et al.

(10) Patent No.: US 12,310,906 B2
(45) Date of Patent: *May 27, 2025

(54) ADJUSTABLE CERVICAL TRACTION ASSEMBLIES FOR PERSON SUPPORT APPARATUSES (71) Applicant: Allen Medical Systems, Inc., Batesville, IN (US)

(72) Inventors: Kyle McKenney, Maynard, MA (US); Andrew David Clark, Waltham, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,375

(22) Filed: Jan. 4, 2024

(65) Prior Publication Data

US 2024/0130916 A1 Apr. 25, 2024

Related U.S. Application Data (62) Division of application No. 17/410,444, filed on Aug. 24, 2021, now Pat. No. 11,903,889, which is a
(Continued)

(51) Int. Cl.
*A61F 5/04* (2006.01)
*A61F 5/042* (2006.01)
(Continued)

(52) U.S. Cl.
CPC ............ *A61H 1/0222* (2013.01); *A61F 5/04* (2013.01); *A61F 5/042* (2013.01); *A61F 5/048* (2013.01);
(Continued)

(58) Field of Classification Search
CPC . A61F 5/04; A61F 5/042; A61F 5/048; A61H 1/0218; A61H 1/0222
See application file for complete search history.

(56) References Cited

U.S. PATENT DOCUMENTS 2,262,271 A 11/1941 DeCamp
4,538,598 A 9/1985 Gill et al.
(Continued)

FOREIGN PATENT DOCUMENTS

CN 204671347 U 9/2015
JP 2002119526 A 4/2002
(Continued)

OTHER PUBLICATIONS

Office Action mailed Mar. 12, 2019 related to Japanese Application No. 2018-012581.
(Continued)

*Primary Examiner* — Victoria Hicks Fisher
(74) *Attorney, Agent, or Firm* — Dinsmore & Shohl LLP (57) ABSTRACT A cervical traction assembly for use with a patient support apparatus includes an adjustment carriage track member including a connecting bracket assembly that releasably connects to a mount support member of the patient support apparatus. The adjustment track member includes a track body including a pair of opposing sidewalls that are spaced-apart from each other to define an elongated channel therebetween. Each sidewall includes a guide track that extends along a length of the respective sidewall. A rope angle adjustment carriage is located within the channel. The rope angle adjustment carriage includes a first track engagement member that is received by one of the guide tracks of one of the sidewalls and a second track engagement member that is received by another of the guide tracks of another of the sidewalls. The first track engagement member has a locked
(Continued)

configuration that inhibits movement of the rope angle adjustment carriage.

8 Claims, 11 Drawing Sheets

Related U.S. Application Data division of application No. 15/878,843, filed on Jan. 24, 2018, now Pat. No. 11,185,459.

(60) Provisional application No. 62/452,749, filed on Jan. 31, 2017.

(51) Int. Cl.
| | |
|---|---|
| *A61F 5/048* | (2006.01) |
| *A61G 7/05* | (2006.01) |
| *A61G 7/07* | (2006.01) |
| *A61G 13/00* | (2006.01) |
| *A61G 13/04* | (2006.01) |
| *A61G 13/12* | (2006.01) |
| *A61H 1/02* | (2006.01) |
| *A61G 7/012* | (2006.01) |
| *A61G 13/06* | (2006.01) |

(52) U.S. Cl.
CPC ............ *A61G 7/05* (2013.01); *A61G 7/072* (2013.01); *A61G 13/009* (2013.01); *A61G 13/04* (2013.01); *A61G 13/121* (2013.01); *A61G 13/1295* (2013.01); *A61H 1/0296* (2013.01); *A61G 7/012* (2013.01); *A61G 13/06* (2013.01); *A61H 2201/5007* (2013.01); *A61H 2203/0468* (2013.01); *A61H 2205/04* (2013.01)

(56) References Cited

U.S. PATENT DOCUMENTS

| | | |
|---|---|---|
| RE32,791 E | 11/1988 | Saunders |
| 4,890,605 A | 1/1990 | Rosendale |
| 11,185,459 B2 * | 11/2021 | McKenney ............ A61F 5/048 |
| 2007/0043115 A1 | 2/2007 | Buchman |
| 2010/0280549 A1 | 11/2010 | Yen |
| 2013/0131570 A1 | 5/2013 | Hoffman et al. |
| 2018/0214333 A1 * | 8/2018 | McKenney ............ A61F 5/048 |

FOREIGN PATENT DOCUMENTS

| | | |
|---|---|---|
| JP | 2002519111 A | 7/2002 |
| JP | 2004337350 A | 12/2004 |
| WO | 2014033633 A2 | 6/2014 |

OTHER PUBLICATIONS

European Extended Search Report for EP Application No. 18153501.4 dated Jun. 4, 2018 (9 pages).

* cited by examiner

ADJUSTABLE CERVICAL TRACTION ASSEMBLIES FOR PERSON SUPPORT APPARATUSES

CROSS-REFERENCE TO RELATED APPLICATIONS

This application is a divisional of U.S. patent application Ser. No. 17/410,444, filed Aug. 24, 2021, which is a divisional of U.S. patent application Ser. No. 15/878,843, filed Jan. 24, 2018, which claims the benefit of and priority to U.S. Provisional Patent Application Ser. No. 62/452,749, filed Jan. 31, 2017, all of which are entitled "Adjustable Cervical Traction Assemblies for Personal Support Apparatuses," the entireties of which are all incorporated by reference herein.

BACKGROUND

Field

The present specification generally relates to person support apparatuses and, more specifically, to person support apparatuses including adjustable cervical traction assemblies.

Technical Background

Cervical traction assemblies may be used for pain relief by applying tension to the cervical region of a person's neck. The cervical traction assemblies may be used with the person in either a horizontal (lying down) or vertical (standing or sitting) orientation. In some instances, it may be desired to apply tension at different angles. The cervical traction assemblies may be adjustable to allow for changes in the tension direction. However, such cervical traction assemblies may have limited adjustability and changing angles may be time-consuming.

Accordingly, a need exists for person support apparatuses that include adjustable cervical traction assemblies.

SUMMARY

In one embodiment, a cervical traction assembly for use with a patient support apparatus includes an adjustment carriage track member including a connecting bracket assembly that releasably connects to a mount support member of the patient support apparatus. The adjustment track member includes a track body including a pair of opposing sidewalls that are spaced-apart from each other to define an elongated channel therebetween. Each sidewall includes a guide track that extends along a length of the respective sidewall. A rope angle adjustment carriage is located within the channel. The rope angle adjustment carriage includes a first track engagement member that is received by one of the guide tracks of one of the sidewalls and a second track engagement member that is received by another of the guide tracks of another of the sidewalls. The first track engagement member has a locked configuration that inhibits movement of the rope angle adjustment carriage along the channel and an unlocked configuration that allows movement of the rope angle adjustment carriage along the channel.

In another embodiment, a person support apparatus includes a forward column assembly including a forward mount assembly connected thereto. The forward mount assembly includes a mount support member that is connected to the forward column assembly. A cervical traction assembly includes an adjustment carriage track member that is mounted to the mount support member. The adjustment track member includes a connecting bracket assembly that releasably connects to a mount support member of the patient support apparatus. The adjustment track member includes a track body including a pair of opposing sidewalls that are spaced-apart from each other to define an elongated channel therebetween. Each sidewall includes a guide track that extends along a length of the respective sidewall. A rope angle adjustment carriage is located within the channel. The rope angle adjustment carriage includes a first track engagement member that is received by one of the guide tracks of one of the sidewalls and a second track engagement member that is received by another of the guide tracks of another of the sidewalls. The first track engagement member has a locked configuration that inhibits movement of the rope angle adjustment carriage along the channel and an unlocked configuration that allows movement of the rope angle adjustment carriage along the channel.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Reference will now be made in detail to embodiments of person support apparatuses that include adjustable cervical traction assemblies. The person support apparatuses may include a support surface that is generally an upper surface of a surgical table, such as a spine table or standard operating room (OR) table. For example, the person support apparatus may include a two-column spine table that includes a forward column assembly and a rearward column assembly. The forward column assembly includes a bracket support assembly including a mount support member that is fixedly mounted to the forward column assembly. A support bracket may be removably mounted to the fixed mount support member. The support bracket may be used to mount the support surface at a desired height and orientation. The adjustable cervical traction assembly may be mounted directly the mount support member, as opposed to the support bracket. Such a mounting arrangement for the adjustable cervical traction assembly can simplify attachment of the adjustable cervical traction assembly to the forward column assembly and facilitate a variety of surgical traction procedures at various tension angles.

As used herein, the term "longitudinal direction" refers to the forward-rearward direction of the person support apparatus (i.e., in the +/−X-direction as depicted). The term "lateral direction" refers to the cross-direction of the person support apparatus (i.e., in the +/−Y-direction as depicted), and is transverse to the longitudinal direction. The term "vertical direction" refers to the upward-downward direction of the person support apparatus (i.e., in the +/−Z-direction as depicted), and is transverse to the lateral and the longitudinal directions. The terms "head end" and "foot end" refer to the relative location of components of the person support apparatus in the longitudinal direction.

Figure 1:
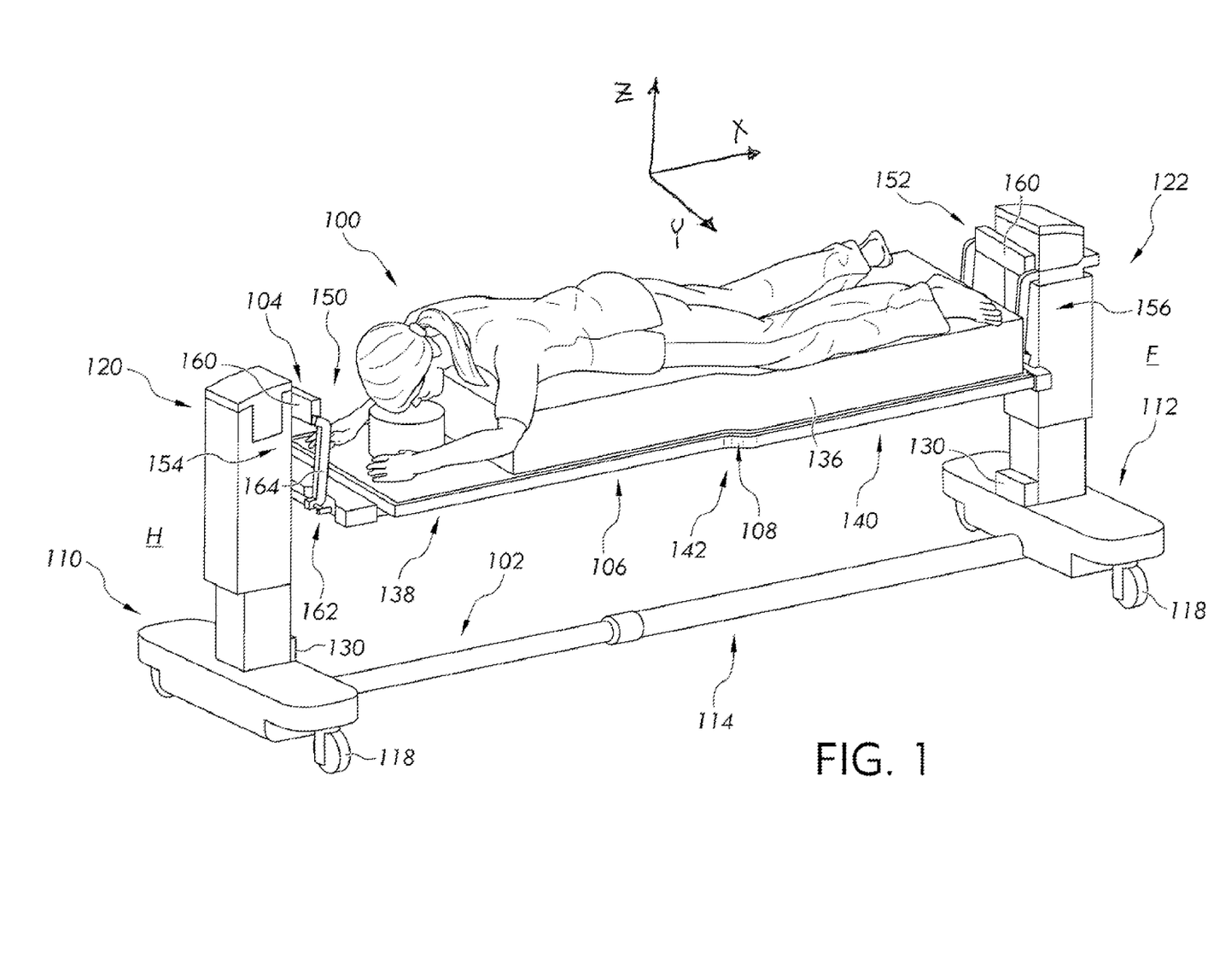
FIG. 1 depicts a perspective view of a person support apparatus according to one or more embodiments shown or described herein.

Referring to FIG. 1, a person support apparatus 100 may be, for example, a two-column operating table. The person support apparatus 100 includes a base frame 102 and a primary support frame 104 that is supported by the base frame 102. A patient support assembly 106 including a longitudinal frame 108 may be removably coupled to the primary support frame 104.

The base frame 102 of the person support apparatus 100 may include a forward portion 110 positioned at a head end of the person support apparatus 100 and a rearward portion 112 positioned at a foot end of the person support apparatus 100. The forward portion 110 and the rearward portion 112 may be spaced-apart from one another in the longitudinal direction and may be coupled to one another by a central portion 114 that extends between the forward portion 110 and the rearward portion 112. The central portion 114 may be extendable and/or retractable in the longitudinal direction, thereby increasing or decreasing the distance between the forward portion 110 and the rearward portion 112 in the longitudinal direction. The central portion 114 may be, for example, a telescoping tube having electrical connectors (e.g., wires) that pass therethrough for carrying power and electrical signals between the forward portion 110 and the rearward portion 112. In some embodiments, the forward portion 110 and the rearward portion 112 are coupled to a plurality of rollers 118, such that the person support apparatus 100 may be moved along a surface, such as a floor.

The primary support frame 104 extends upwardly from the base frame 102. In the embodiment depicted in FIG. 1, the primary support frame 104 includes a forward column assembly 120 that extends from the forward portion 110 of the base frame 102 in the vertical direction. The primary support frame 104 includes a rearward column assembly 122 that extends from the rearward portion 112 of the base frame 102 in the vertical direction. The forward column assembly 120 is positioned at the head end of the person support apparatus 100 and the rearward column assembly 122 is positioned at the foot end of the person support apparatus 100, and the forward column assembly 120 is spaced-apart from the rearward column assembly 122 in the longitudinal direction.

The forward column assembly 120 and the rearward column assembly 122 may be adjustable in the vertical direction such that the forward column assembly 120 and the rearward column assembly 122 may raise or lower the patient support assembly 106, which can be used to reposition or change a position of a patient. In embodiments, at least one column assembly actuator 130 is coupled to the forward column assembly 120 and/or the rearward column assembly 122 and can move the forward column assembly 120 and the rearward column assembly 122 upward and downward in the vertical direction with respect to the base frame 102. The column actuator 130 may be a powered actuator, such as an electric motor or the like, or may be a manually powered, such as by a foot pedal, a crank, or the like. The column actuator 130 may include a linear actuator, such as a screw, a wheel and axle, a cam, a hydraulic actuator, a pneumatic actuator, a piezoelectric actuator, an electro-mechanical actuator, or the like.

Figure 2:
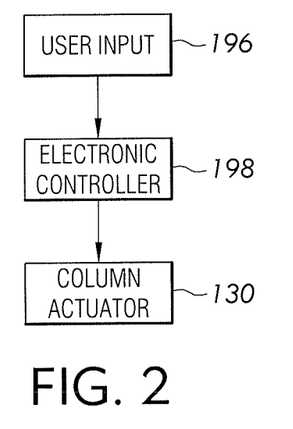
FIG. 2 illustrates a block diagram of a control system for the person support apparatus of FIG. 1 according to one or more embodiments shown or described herein.

Referring to FIG. 2, in embodiments where the column actuator 130 includes an electric motor, the column actuator 130 may be communicatively coupled to an electronic controller 198. The electronic controller 198 includes a processor and a memory storing computer readable and executable instructions, which, when executed by the processor, facilitate operation of the column actuator 130. In particular, the electronic controller 198 can send a signal to the at least one column actuator 130 to raise or lower the forward column assembly 120 and/or the rearward column assembly 122 in the vertical direction. A user input 196 is communicatively coupled to the electronic controller 198. The user input 196 may include a device that allows a user to input various parameters into the electronic controller 198 to facilitate operation of the person support apparatus 100.

For example, a healthcare professional may utilize the user input 196 to send a signal to the electronic controller 198 to command the at least one actuator 130 to raise or lower the forward column assembly 120 and/or the rearward column assembly 122 in the vertical direction. In embodiments, the user input 196 may include various user input devices, including, but not limited to, graphical user interfaces (GUIs), keyboards, pendants, or the like.

Referring again to FIG. 1, the forward column assembly 120 and the rearward column assembly 122 may be raised and lowered in the vertical direction independent of one another such that the patient support assembly 106 may be tilted with respect to the horizontal plane (i.e., the X-Y plane as depicted). For example, the forward column assembly 120 may be raised with respect to the rearward column assembly 122 in the vertical direction such that the head end of the patient support assembly 106 is positioned higher than the foot end of the patient support assembly 106 in the vertical direction (i.e., a reverse Trendelenburg position). Conversely, the rearward column assembly 122 may be raised with respect to the forward column assembly 120 in the vertical direction, such that the foot end of the patient support assembly 106 is positioned higher than the head end of the patient support assembly 106 in the vertical direction (i.e., a Trendelenburg position). In embodiments, both the forward column assembly 120 and the rearward column assembly 122 may be raised or lowered in the vertical direction simultaneously, thereby raising both the head end and the foot end of the patient support assembly 106.

The patient support assembly 106 may include a support surface 136 that includes one or more segments positioned between the forward column assembly 120 and the rearward column assembly 122 in the longitudinal direction to support a patient on the person support apparatus 100. The support surface 136 may be formed of a radiolucent material such as carbon fiber or other non-metallic materials, so that the patient support assembly 106 does not interfere with medical imaging of a patient such as x-rays or other medical imaging. The patient support assembly 106 may include, for example, a head segment 138 positioned at the head end of the person support apparatus 100 which supports the upper body and/or the head and arms of a patient. The patient support assembly 106 may further include a leg segment 140 positioned at the foot end of the person support apparatus 100 which supports the lower body and/or the legs of a patient. The patient support assembly 106 may also include a torso segment 142 that is positioned between the head segment 138 and the leg segment 140 in the longitudinal direction which supports a torso and/or a mid-section of a patient. The head segment 138, leg segment 140 and torso segment 142 may all be a single component or, in other embodiments, the head segment 138, leg segment 140 and torso segment 142 may be one or more articulating components capable of movement relative to others of the components, for example, to place the patient in a desired position.

The patient support assembly 106 may be removably coupled to the forward and rearward column assemblies 120 and 122 by a forward patient support deck connecting device 150 and a rearward patient support deck connecting device 152, respectively. As an example, the forward patient support deck connecting device 150 may be releasably connected to a forward mount assembly 154 (e.g., including an H-bracket) that is, in turn, connected to the forward column assembly 120. Likewise, the rearward patient support deck connecting device 152 may be releasably connected to a rearward mount assembly 156 (e.g., including an H-bracket) that is, in turn, connected to the rearward column assembly 122.

The forward mount assembly 154 and the rearward mount assembly 156 may each include a mount support member 160 that is mounted to the forward column assembly 120 and the rearward column assembly 122. In some embodiments, the mount support member 160 is fixed to the forward column assembly 120 and the rearward column assembly 122. As used herein, the term "fixed" in relation to the mount support member 160 means that the mount support member 160 is not intended to be readily removable from the associated forward and rearward column assembly 120 and 122 under normal operating conditions. This is because the mount support member 160 can provide a structure that supports a mounting bracket 162. In the illustrated embodiment, the mounting bracket 162 is an H-bracket that includes a pair of mount arms 164 and 166 (FIG. 3) for mounting various structures, such as the patient support assembly 106.

Figure 3:
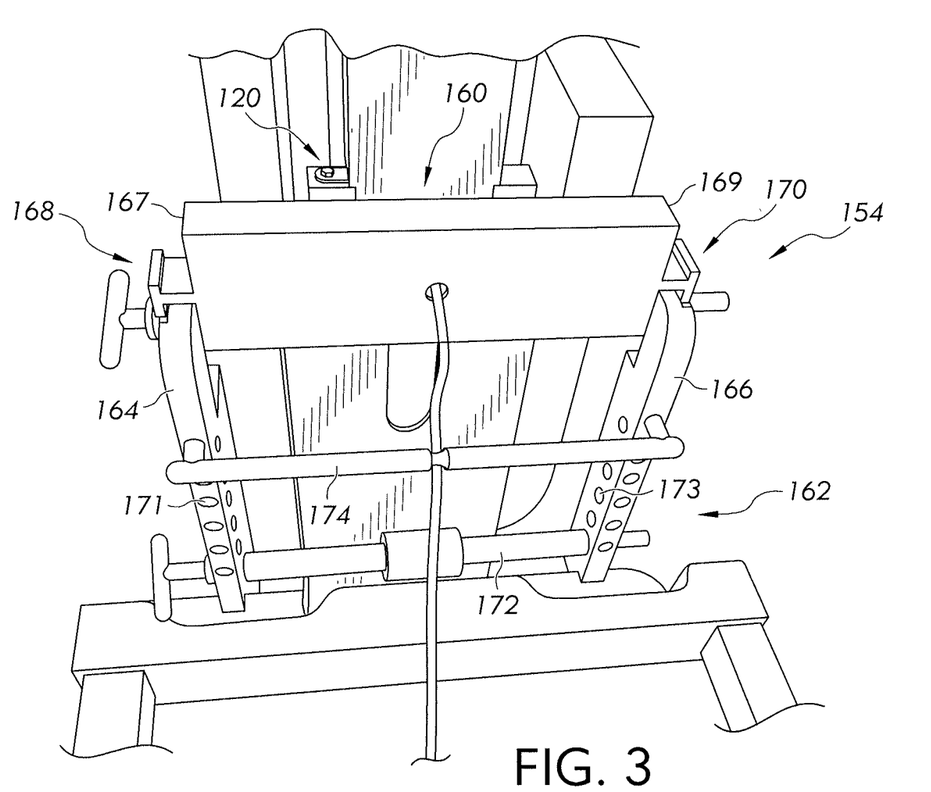
FIG. 3 illustrates a forward mount assembly of the person support apparatus of FIG. 1 according to one or more embodiments shown or described herein.

Referring to FIG. 3, a more detailed view of the forward mount assembly 154 is illustrated. The forward mount assembly 154 and the rearward mount assembly 156 may include the same or similar components. Thus, only the forward mount assembly 154 is described in detail for clarity. The forward mount assembly 154 may include the mount support member 160 (sometimes referred to as a bowtie) that is fixedly mounted to the forward column assembly 120. The mount support member 160 includes mount structures 168 and 170 that are located at opposite ends 167 and 169 for receiving the mount arms 164 and 166 of the mounting bracket 162 such that the mount arms 164 and 166 hang from the mount support member 160 in a vertical orientation. Each mount arm 164 and 166 includes a column of laterally facing openings 173 and longitudinally facing openings 171. The laterally facing openings 173 of the mount arms 164 and 166 generally face each other and are each substantially aligned vertically and horizontally so that a support rod 172 can pass therethrough, e.g., for mounting a device. The longitudinally facing openings 171 of the mount arms 164 and 166 generally face in the longitudinal direction and are also aligned vertically and horizontally. This can allow additional rods 174 or other devices to be mounted therein.

Figure 4:
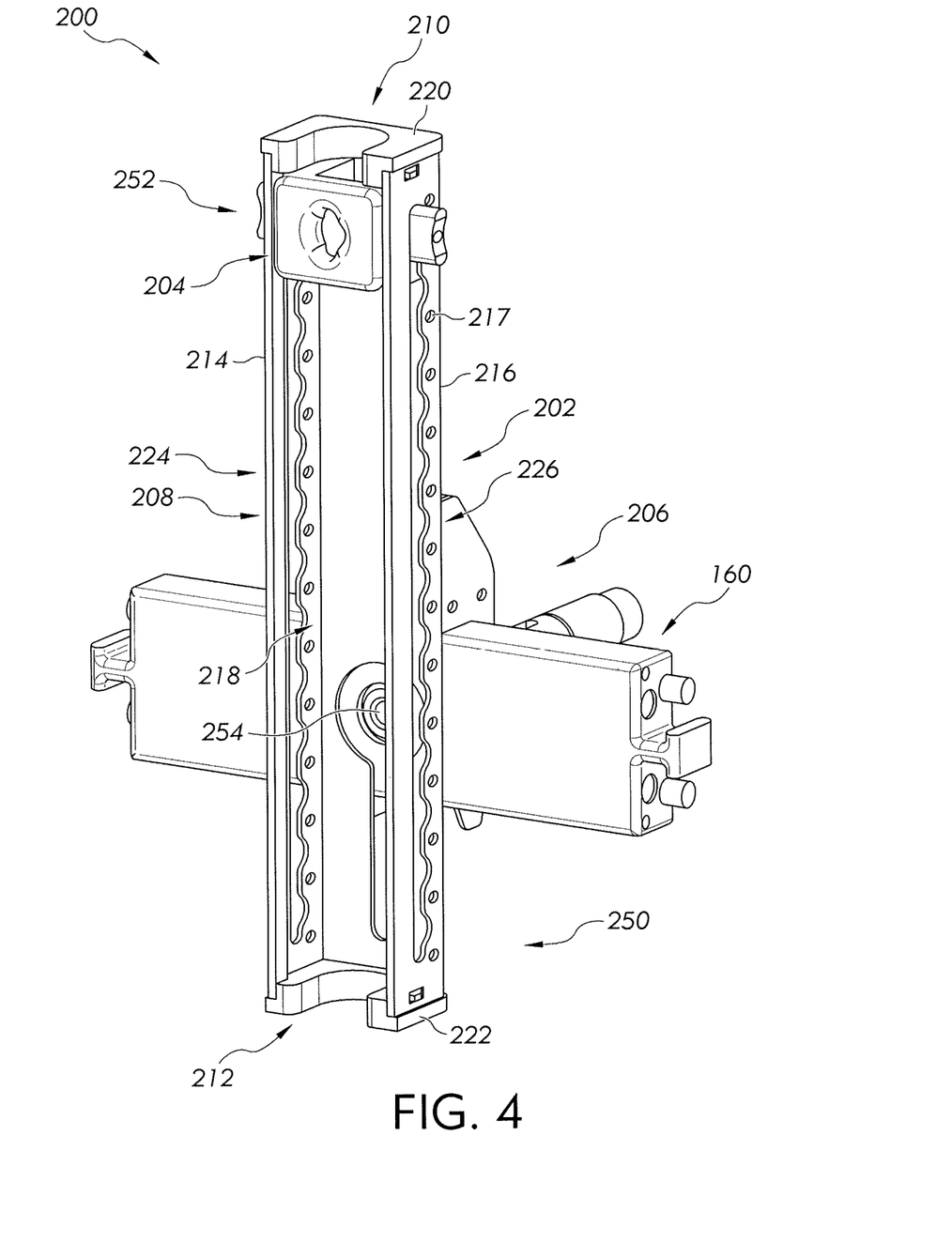
FIG. 4 illustrates an adjustable cervical traction assembly for the person support apparatus of FIG. 1 according to one or more embodiments shown or described herein.
Figure 5:
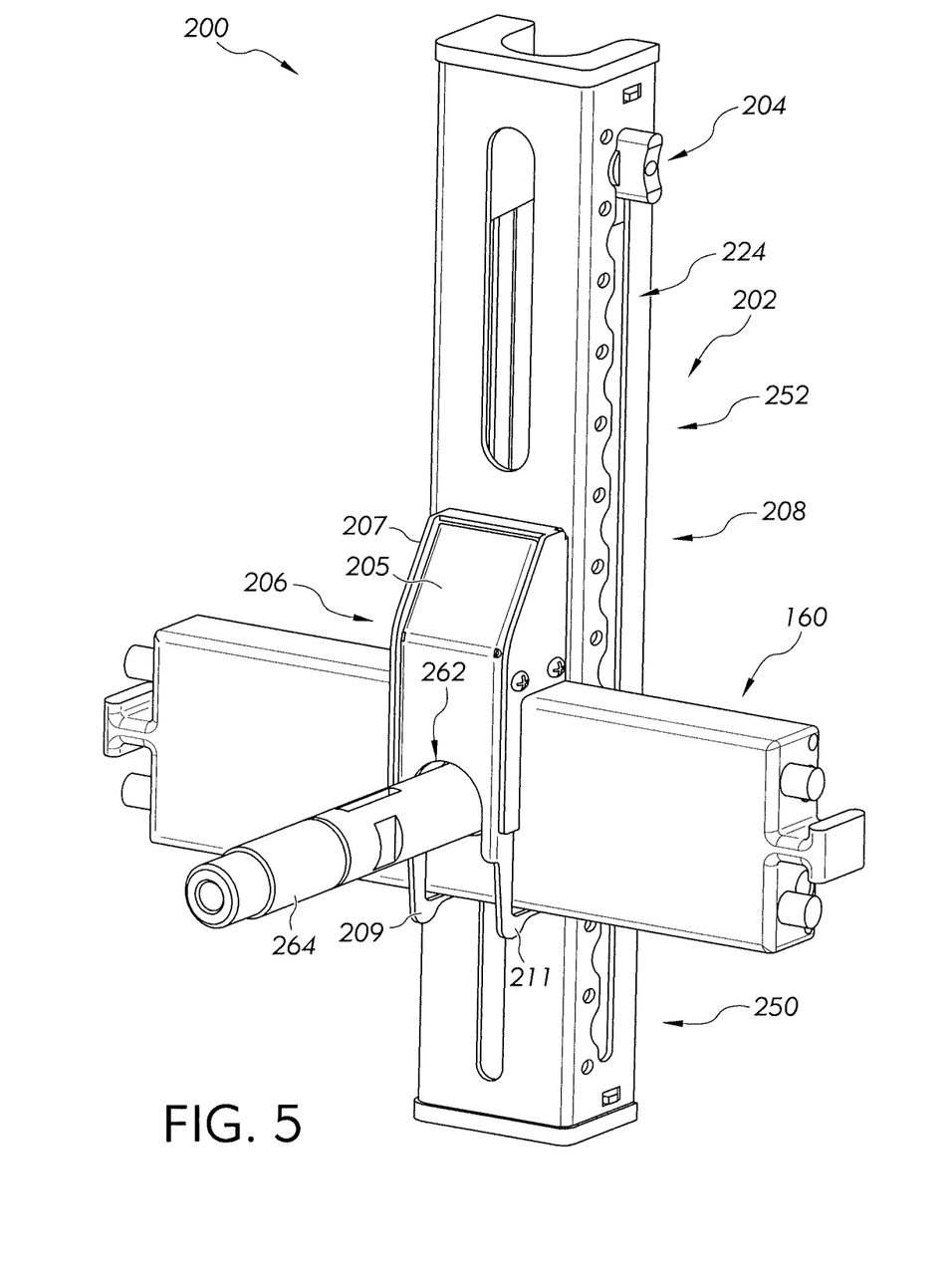
FIG. 5 illustrates another view of the adjustable cervical traction assembly of FIG. 4 according to one or more embodiments shown or described herein.

Referring to FIGS. 4 and 5, an adjustable cervical traction assembly 200 is illustrated connected to the mount support member 160 with the mount support member 160 detached from the forward column assembly 120 for clarity. The cervical traction assembly 200 includes an adjustment carriage track member 202 and a rope angle adjustment carriage 204. The adjustment carriage track member 202 includes a connecting bracket assembly 206 that releasably connects to the mount support member 160 and a track body 208 that is oriented substantially vertically with the connecting bracket assembly 206 connected to the mount support member 160. FIG. 5 illustrates the connecting bracket assembly 206, which includes an actuatable latch 205 that is moveable connected to a latch housing 207. The actuatable latch 205 can be used to move a pair of connecting arms 209 and 211 between latched and unlatched configurations.

Referring particularly to FIG. 4, the track body 208 is generally U-shaped having an upper end 210 and a lower end 212 that is opposite the upper end 210. Pair of sidewalls 214 and 216 extend between the upper end 210 and the lower end 212 that are spaced-apart from each other thereby defining a carriage channel 218 therebetween. The upper end 210 and lower end 212 may include an end cap 220 and 222 that at least partially closes or otherwise caps the upper and lower ends 210 and 212.

Each sidewall 214 and 216 includes a guide track 224, 226. The guide tracks 224 and 226 may be formed as shaped slots that extend through the sidewalls 214 and 216. As will be described in greater detail below, the guide tracks 224 and 226 are shaped to allow for movement of the rope angle adjustment carriage 204 along a height of the carriage channel 218.

Figure 6:
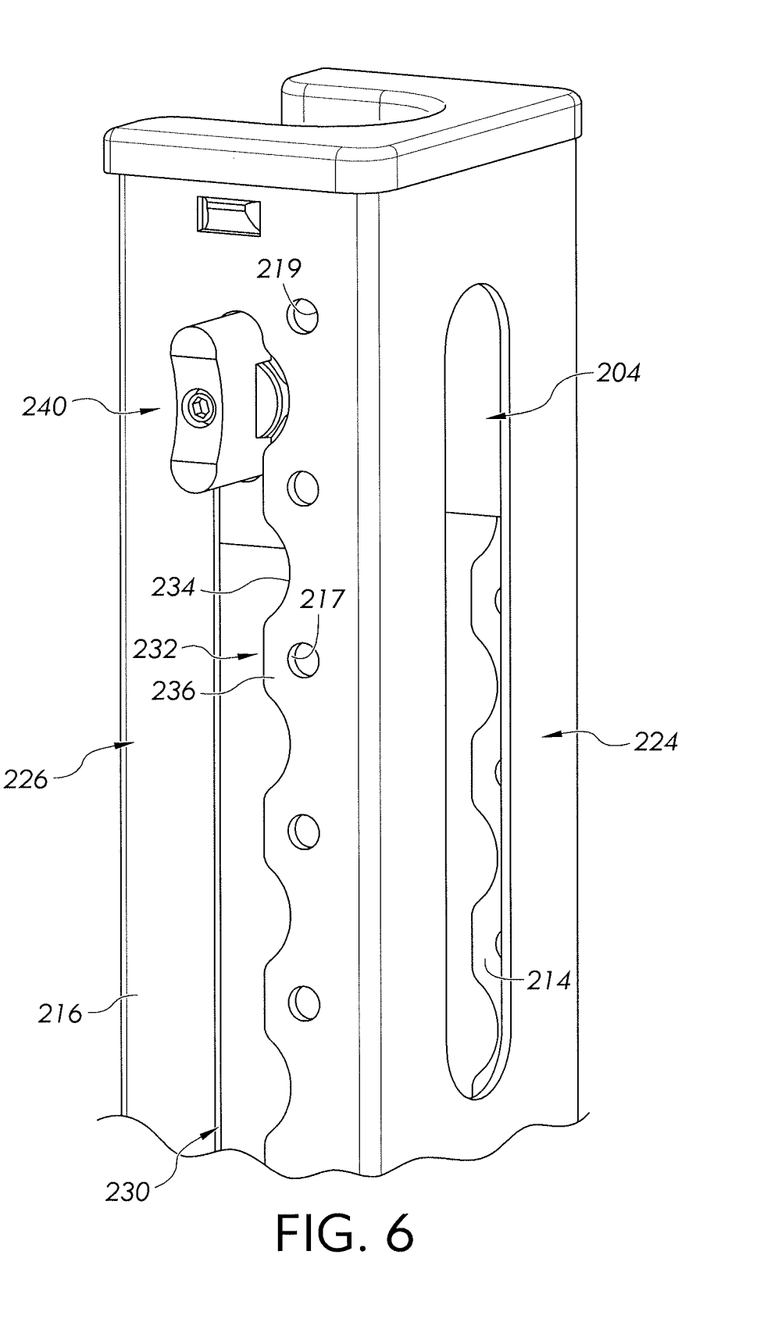
FIG. 6 illustrates a detail view of the cervical traction assembly of FIG. 4 according to one or more embodiments shown or described herein.

FIG. 6 illustrates the guide track 226 of the sidewall 216 in greater detail. The guide track 226 has a first side 230 that is substantially flat or linear and an opposite, second side 232 having undulating valleys 234 and peaks 236. The valleys 234 provide regions of increased slot width, while the peaks 236 provide regions of decreased slot width. The rope angle adjustment carriage 204 may include a pair of depressible track engagement members 238 and 240 (FIG. 4) in the form of buttons that, in their extended positions, can lock the rope angle adjustment carriage 204 at a desired height along the guide tracks 224 and 226.

Figure 7:
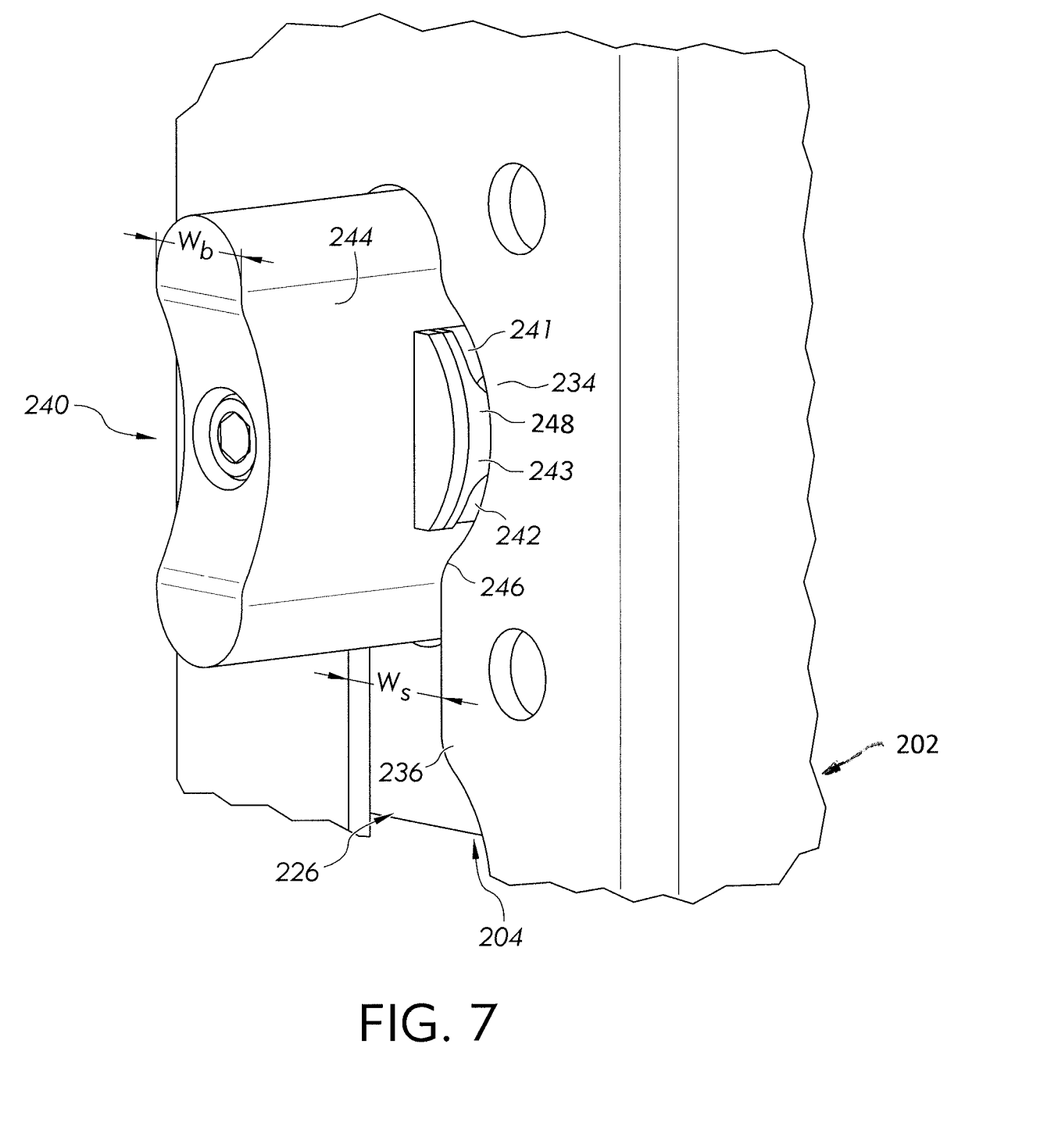
FIG. 7 illustrates a more detail view of the cervical traction assembly of FIG. 4 according to one or more embodiments shown or described herein.

Referring to FIG. 7, the depressible track engagement member 240 includes a body 244 having a width Wb that is sized to slide through the reduced slot width Ws at the peaks 236 of the guide track 226. An engagement projection 248 is provided on the body 244 that increases the width of the body 244. With the track engagement member 240 in the extended configuration as shown, the engagement projection 248 is received within the valley 234 of the guide track 226, thereby increasing the width of the body within the guide track 226 and preventing movement of the track engagement member 240 beyond the regions of decreased slot widths provided by the peaks 236. Such an arrangement can be used to lock the rope angle adjustment carriage 204 at a particular location along the height of the adjustment carriage track member 202. In some embodiments, the engagement projection 248 may include recessed regions 241 and 242 that are formed in a perimeter 243 of the engagement projection 248. The recessed regions 241 and 242 can be used to receive an edge 246 of the guide track 226 at the peaks 236. With the edge 246 of the track member 226 engaged with one of the recessed regions 241, 242, the track engagement member 240 may be inhibited from actuating from the extended configuration without further physical movement of the rope angle adjustment carriage 204 to remove the edge 246 of the guide track 226 from the recessed region 241, 242.

Referring again to FIGS. 4 and 5, the rope angle adjustment carriage 204 may be adjusted to a variety of heights along the adjustment carriage track member 202. In some embodiments, the sidewalls 214 and 216 may include locking position openings 217 that can receive a spring-loaded ball 219 (FIG. 6), which can provide an audible indication at each potential locking position. In the illustrated example, the connecting bracket assembly 206 is located along a height of the track body 208, such that a lower portion 250 of the guide tracks 224, 226 is located below the mount support member 160 and an upper portion 252 of the guide tracks 224, 226 is located above the mount support member 160. In particular, the mount support member 160 may include a rope pass-through opening 254 through which a rope, cable etc. may pass through for applying a tension force. The guide tracks 224, 226 may be provided both above and below the rope pass-through opening 254 to adjust the tension angle either above or below the rope pass-through opening 254.

Figure 8:
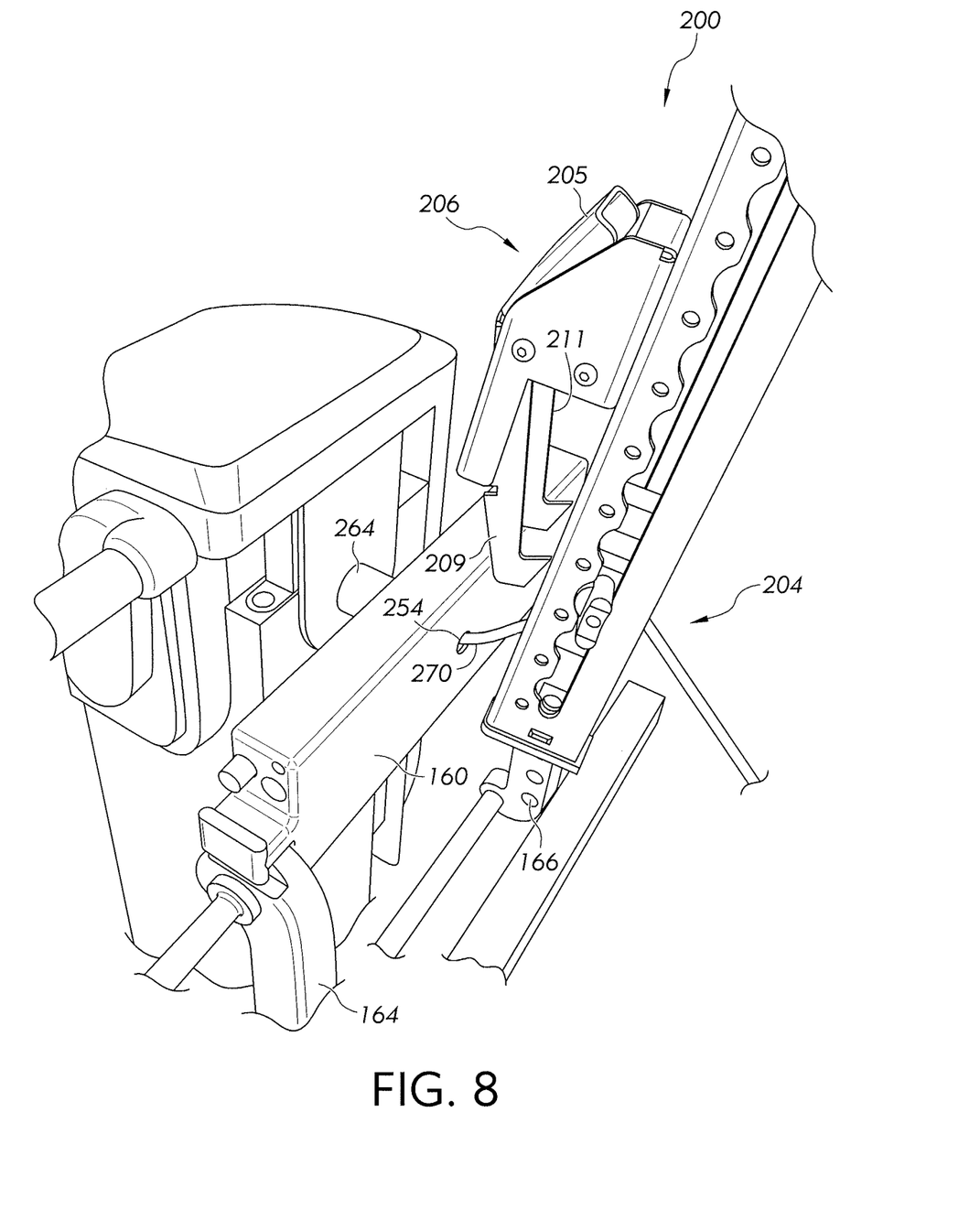
FIG. 8 illustrates a method of mounting the cervical traction assembly of FIG. 4 to the patient support apparatus of FIG. 1 according to one or more embodiments shown and described herein.
Figure 9:
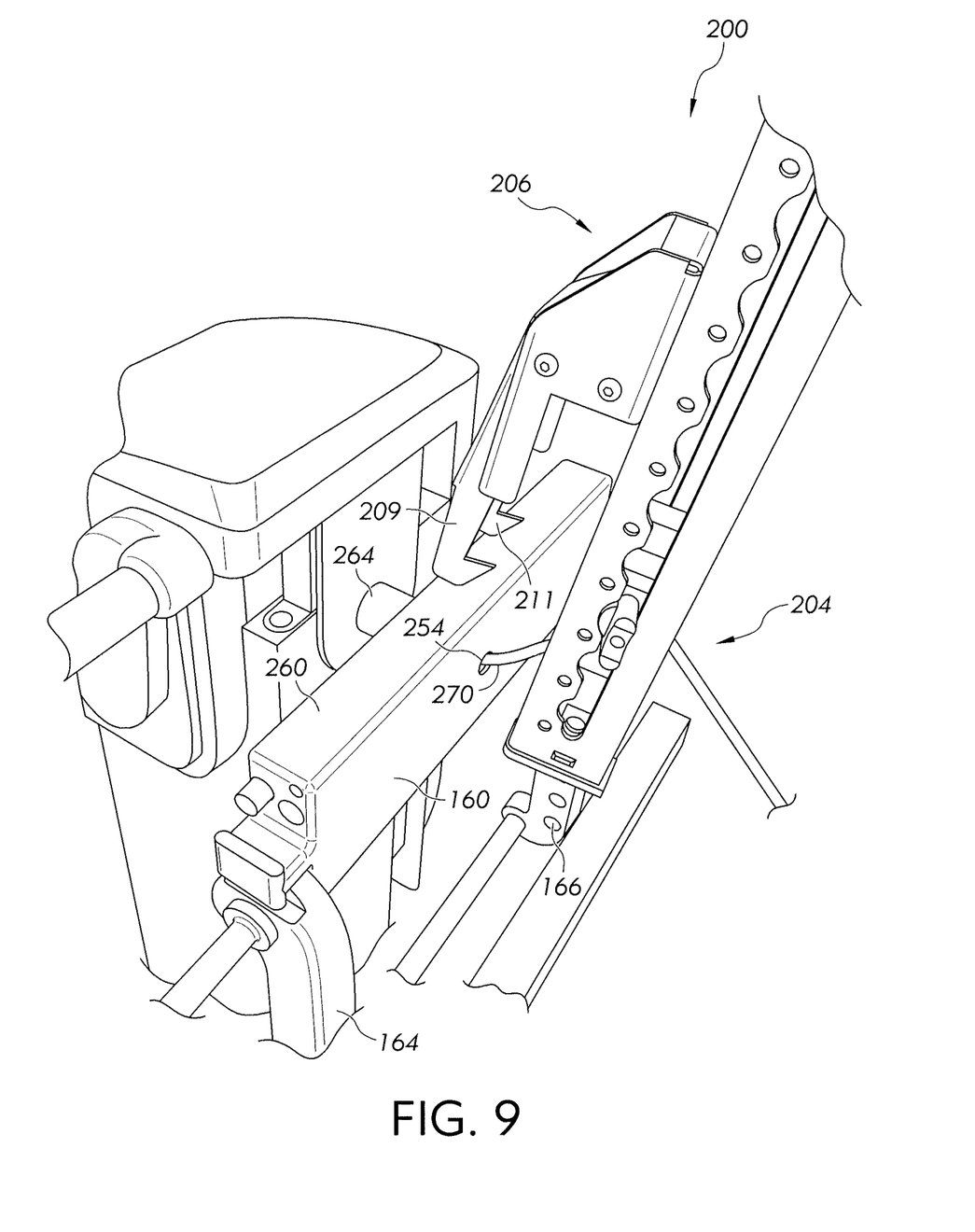
FIG. 9 illustrates a method of mounting the cervical traction assembly of FIG. 4 to the patient support apparatus of FIG. 1 according to one or more embodiments shown and described herein.
Figure 10:
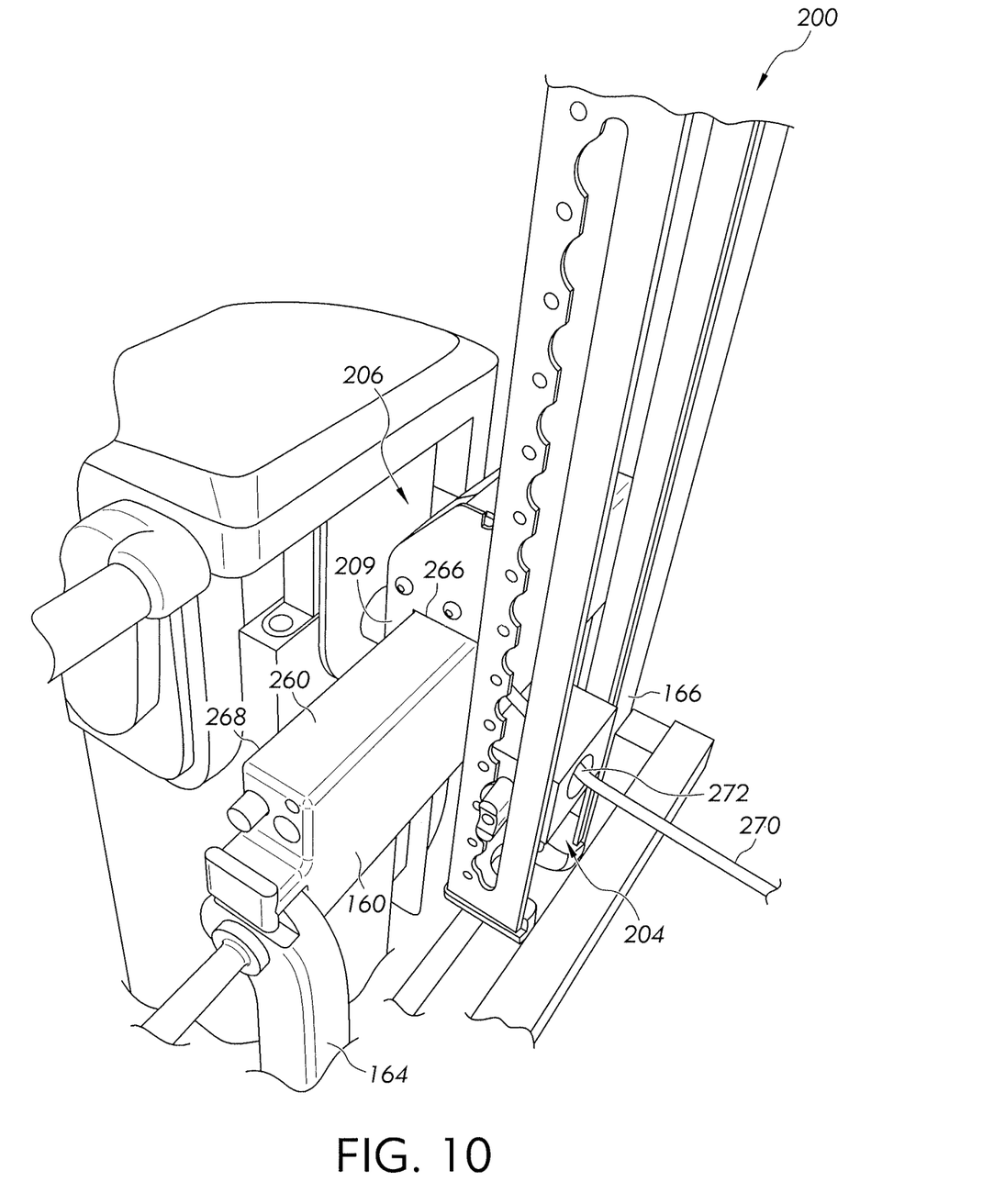
FIG. 10 illustrates a method of mounting the cervical traction assembly of FIG. 4 to the patient support apparatus of FIG. 1 according to one or more embodiments shown and described herein.

Referring to FIGS. 8-10, the adjustable cervical traction assembly 200 may be mounted to the mount support member 160 using the connecting bracket assembly 206. Referring first to FIG. 8, the mount support member 160 is illustrated attached to the forward column assembly 120. The mounting bracket 162 including the mount arms 164 and 166 may or may not be attached to the mount support member 160 as described above. The operator may manually grasp the connecting bracket assembly 206 and actuate the actuatable latch 205. Depressing the actuatable latch 205 can move the connecting arms 209 and 211 from a closed position, not allowing the cervical traction assembly 200 to be mounted to the mount support member 160 to an open position, allowing the cervical track assembly to be connected to the mount support member 160.

Referring to FIG. 9, the mounting bracket 162 may be positioned over an upper edge 260 of the mount support member 160 with the mounting bracket 162 in the open configuration. As can be more clearly seen by FIG. 5, the connecting arms 209 and 211 may be spaced-apart in the lateral direction to provide a slot 262 that can receive a mounting rod 264 of the mount support member 160. Such an arrangement can guide the mounting bracket 162 to a vertical centerline at which the mounting rod 264 is located. This can also align the rope angle adjustment carriage 204 with the rope pass-through opening 254 of the mount support member 160 in the lateral direction. Referring to FIG. 10, a square edge 266 of the mounting bracket 162 can engage the upper edge 260 and front surface 268 of the mounting bracket 162 to locate the cervical traction assembly 200 in an upright, vertical orientation.

As can be seen by FIGS. 8-10, a cable or rope 270 may be threaded through the rope pass-through opening 254 of the mount support member 160. During or even after mounting the cervical traction assembly 200 to the mount support member 160, the rope 270 may be threaded through another rope pass-through opening 272 of the rope angle adjustment carriage 204.

Figure 11:
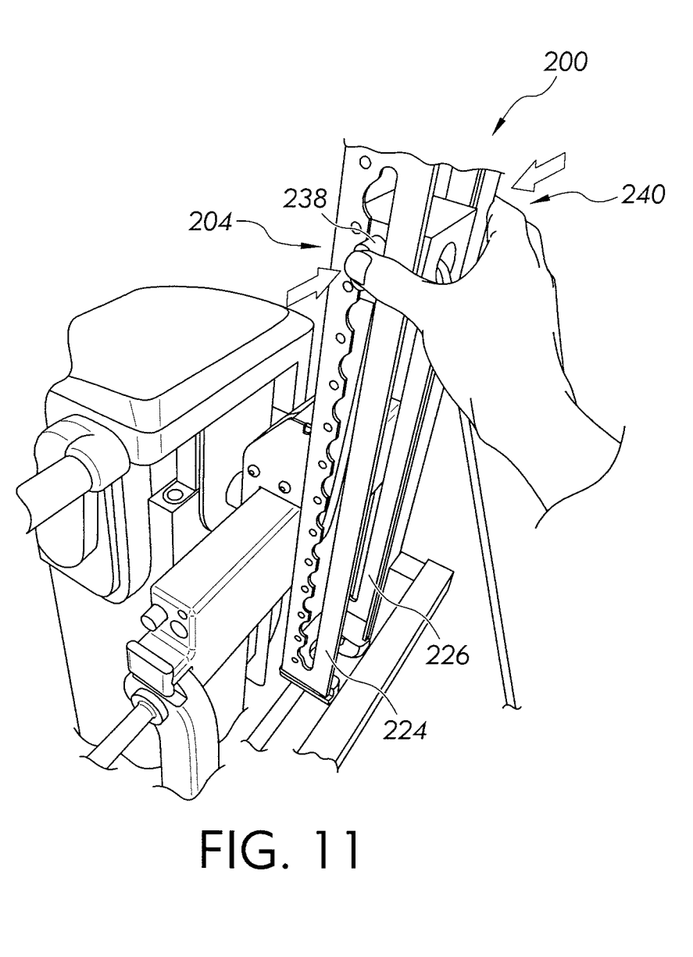
FIG. 11 illustrates a method of adjusting a position of a rope adjustment carriage of the cervical traction assembly of FIG. 4 according to one or more embodiments shown and described herein.
Figure 12:
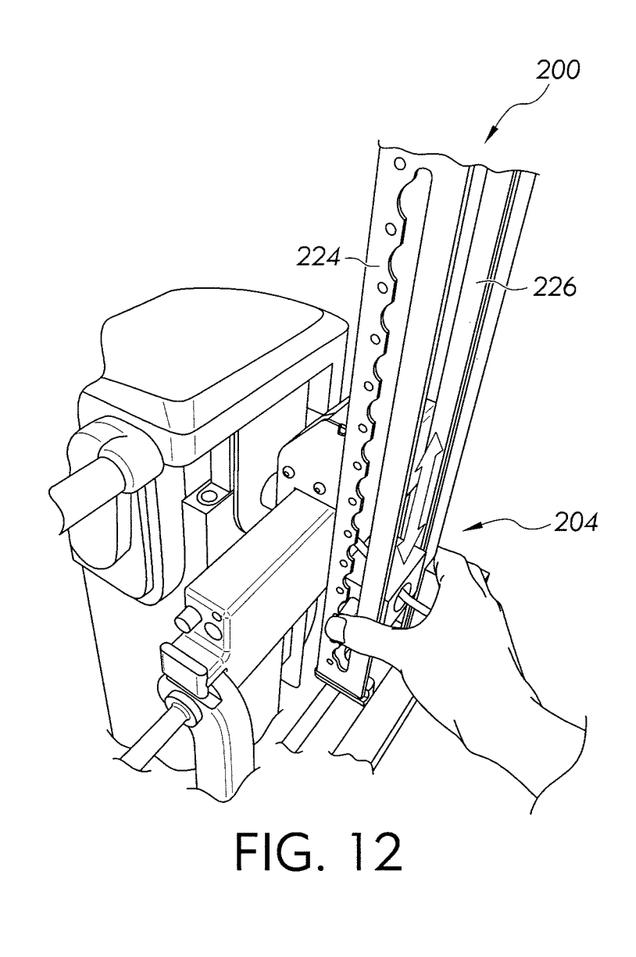
FIG. 12 illustrates another method of adjusting a position of a rope adjustment carriage of the cervical traction assembly of FIG. 4 according to one or more embodiments shown and described herein.

Referring to FIG. 11, the vertical position of the rope angle adjustment carriage 204 may be adjust by depressing the track engagement members 238 and 240. In some embodiments, both the track engagement members 238 and 240 must be depressed to allow for vertical adjustment of the rope angle adjustment carriage 204. As described above with regard to FIG. 7, depressing the track engagement members 238 and 240 moves the engagement projections 248 out of alignment with their respective guide tracks 224 and 226 thereby allowing movement of the track engagement members 238 and 240 within the guide tracks 224 and 226. FIG. 11 illustrates the rope angle adjustment carriage 204 in a raised position while FIG. 12 illustrates the rope angle adjustment carriage 204 in a lowered position.

Figure 13:
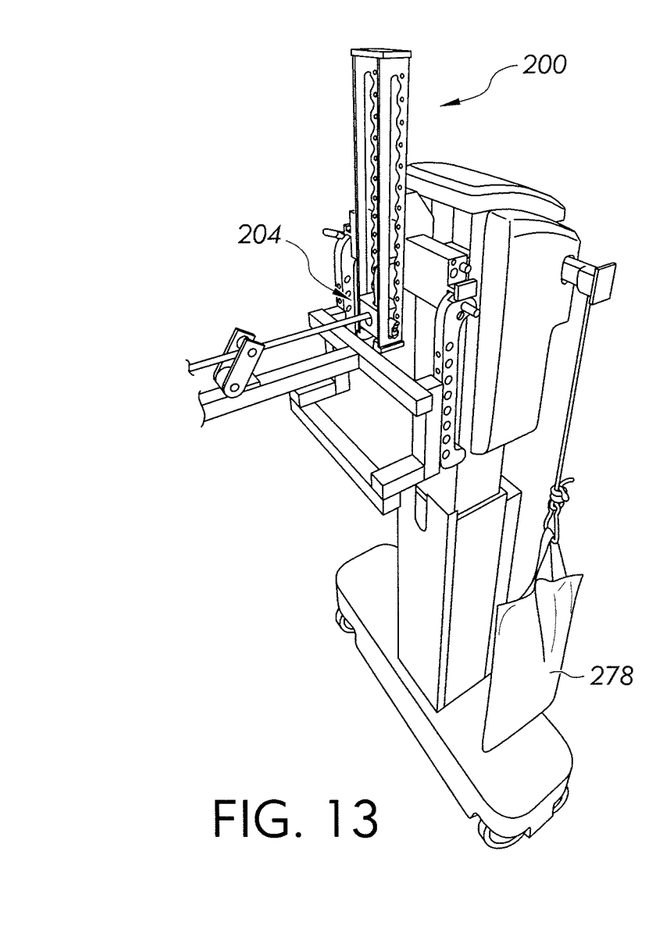
FIG. 13 illustrates a method of adjusting a traction angle using a rope adjustment carriage of the cervical traction assembly of FIG. 4 according to one or more embodiments shown and described herein.
Figure 14:
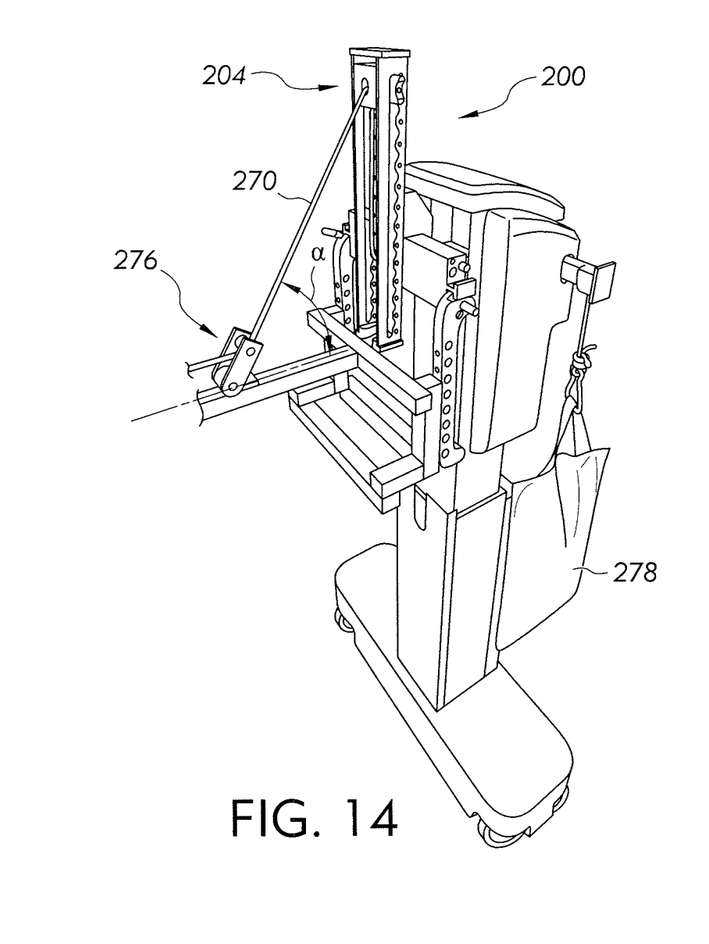
FIG. 14 illustrates another method of adjusting a traction angle using the rope adjustment carriage of the cervical traction assembly of FIG. 4 according to one or more embodiments shown and described herein.

FIGS. 13 and 14 illustrate the cervical traction assembly 200 in operation. Referring first to FIG. 13, the rope angle adjustment carriage 204 is illustrated in a lowered position that may be substantially aligned with a headform bracket 276 that represents an attachment location with a head traction harness. Such an arrangement can provide a tension force (e.g., using weight 278) in a plane that is substantially parallel with a patient body. In some examples, it may be desirable to change the tension angle from substantially horizontal as illustrated by FIG. 13 to include a more vertical component. Referring to FIG. 14, raising the rope angle adjustment carriage 204 can also change the tension angle α from a substantially horizontal tension angle to a nonhorizontal tension angle. In some embodiments, the tension angle α may be adjustable from about −45 degrees to about 75 degrees.

The above-described cervical traction assemblies can be mounted directly to the mount support member, instead of directly to the mounting bracket, such as an H-bracket that is connected to the mount support member. The rope angle adjustment carriage of the cervical traction assemblies can be repositioned both above and below the rope pass through opening of the mount support member in order to achieve a variety of tension angles based on patient needs. The cervical traction assemblies may be readily removable from the mount support member using the connecting bracket assembly that is used to removably mount the cervical traction assemblies to the mount support members.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A cervical traction assembly for use with a patient support apparatus, the cervical traction assembly comprising:
   an adjustment carriage track member that mounts to a mount support member of a forward column assembly of the patient support apparatus, the adjustment carriage track member comprising a track body comprising an elongated channel and a guide track that extends along a length of the elongated channel; and
   a rope angle adjustment carriage that is located within the elongated channel, the rope angle adjustment carriage comprising a track engagement member comprising an engagement projection received by the guide track;
   wherein the track engagement member has a locked configuration that inhibits movement of the rope angle adjustment carriage along the elongated channel and an unlocked configuration that allows movement of the rope angle adjustment carriage along the elongated channel.

2. The cervical traction assembly of claim 1, wherein the guide track is a first guide track, the first guide track having a first side and second side opposing the first side, the second side having undulating peaks and valleys that provide the first guide track with regions of decreased and increased width.

3. The cervical traction assembly of claim 2, wherein the track engagement member comprises:
   a body; and
   the engagement projection that extends a width of the body;
   wherein the track engagement member is moveable between the locked configuration with the engagement projection received within one of the valleys of the first guide track to prevent movement of the track engagement member along the first guide track and the unlocked configuration with the engagement projection removed from the one of the valleys of the first guide track to allow movement of the track engagement member along the first guide track.

4. The cervical traction assembly of claim 3, wherein the adjustment carriage track member comprises a second guide track that extends along a length of the elongated channel, the second guide track having a first side and second side opposing the first side of the second guide track, the second side of the second guide track having undulating peaks and valleys that provide the second guide track with regions of decreased and increased width.

5. The cervical traction assembly of claim 4, wherein the rope angle adjustment carriage comprises a second track engagement member comprising:
   a body; and
   an engagement projection that extends a width of the body;
   wherein the second track engagement member is moveable between a locked configuration with the engagement projection of the second track engagement member received within one of the valleys of the second guide track to prevent movement of the second track engagement member along the second guide track and an unlocked configuration with the engagement projection of the second track engagement member removed from the one of the valleys of the second guide track to allow movement of the second track engagement member along the second guide track.

6. The cervical traction assembly of claim 5, wherein the first track engagement member is a first track engagement member, wherein the first track engagement member and the second track engagement member are configured to be depressed to their unlocked configurations.

7. The cervical traction assembly of claim 6, wherein the body of the first track engagement member includes a recessed region that engages an edge of the first guide track with the first track engagement member in the locked configuration.

8. The cervical traction assembly of claim 1, wherein the rope angle adjustment carriage has a rope pass-through opening.

* * * * *